United States Patent
Richard et al.

(10) Patent No.: US 10,265,048 B2
(45) Date of Patent: Apr. 23, 2019

(54) INTERCHANGEABLE PROBES FOR PORTABLE MEDICAL ULTRASOUND SCANNING SYSTEMS

(71) Applicant: Sonoscanner SARL, Paris (FR)

(72) Inventors: Bruno Richard, Paris (FR); Etienne Richard, Paris (FR); Pierre-Adrien Nadal, Paris (FR)

(73) Assignee: SONOSCANNER SARL, Paris (FR)

( * ) Notice: Subject to any disclaimer, the term of this patent is extended or adjusted under 35 U.S.C. 154(b) by 506 days.

(21) Appl. No.: 14/872,655

(22) Filed: Oct. 1, 2015

(65) Prior Publication Data

US 2017/0095228 A1  Apr. 6, 2017

(51) Int. Cl.
*A61B 8/00* (2006.01)

(52) U.S. Cl.
CPC .......... *A61B 8/4411* (2013.01); *A61B 8/4427* (2013.01); *A61B 8/4433* (2013.01); *A61B 8/4438* (2013.01); *A61B 8/4455* (2013.01); *A61B 8/4488* (2013.01); *A61B 8/461* (2013.01); *A61B 8/4477* (2013.01)

(58) Field of Classification Search
CPC ................................ A61B 8/44; A61B 8/4411
See application file for complete search history.

(56) References Cited

U.S. PATENT DOCUMENTS

| 5,492,126 | A | * | 2/1996 | Hennige | .................. | A61B 8/12 600/439 |
| 2003/0125629 | A1 | * | 7/2003 | Ustuner | ................... | A61B 8/00 600/459 |
| 2010/0249598 | A1 | * | 9/2010 | Smith | ....................... | A61B 8/00 600/459 |

* cited by examiner

*Primary Examiner* — Tse W Chen
*Assistant Examiner* — Jason M Ip
(74) *Attorney, Agent, or Firm* — Greer, Burns & Crain, Ltd.

(57) ABSTRACT

A portable ultrasound scanning system for performing a diagnostic ultrasound scanning process of a patient. The system comprises a portable housing containing ultrasound electronics of a complete ultrasound scanning system including a beamformer that regulate and control operation of the scanning system. A user interface is accessible at the housing. A cable is attached at one end to the housing and at a second end has a connector. An interchangeable probe having a plurality of piezoelectric transducer elements is interchangeably coupled to the connector for transmitting electrical signals between the ultrasound electronics in the housing and the transducer elements of the interchangeable probe.

18 Claims, 4 Drawing Sheets

INTERCHANGEABLE PROBES FOR PORTABLE MEDICAL ULTRASOUND SCANNING SYSTEMS

FIELD OF THE DISCLOSURE

The present disclosure generally relates to portable medical scanners having probes, and in particular relates to a portable medical ultrasound scanning system with interchangeable probes.

BACKGROUND OF THE INVENTION

Conventional medical scanners, such as ultrasound scanning systems, provide two- or three-dimensional images of tissues without subjecting patients to ionizing radiation. These conventional scanners typically comprise a control system, a user interface (e.g., a keyboard, control panel, trackball, and the like), several probes (e.g., transducers or scanheads), a video display, a recording device, and a power system. Generally, ultrasound refers to sound waves emitted at frequencies above the range of human hearing. For diagnostic imaging, frequencies ranging from 2 to 15 megahertz are typically used.

To obtain desired scanned images of different portions of the human body, or other object of interest, it is necessary to use different probes that have different penetration characteristics and different shapes. Full-sized ultrasound scanning systems (desk mounted or cart mounted) generally are provided with a number of sockets for receiving cable connectors for different ultrasound probes that may be used for scanning different portions of a human body or other objects of interest. The probes provided for full-sized systems are provided with a large number, such as 128 or 256, of transducer elements to provide a high resolution scan image. Generally, each transducer element is connected by a separate channel or wire to the ultrasound electronics for conversion into the display image. Thus, the cables connecting the probes to the ultrasound electronics housing typically contain hundreds of shielded wires for the transducer element signals, as well as wires for electrical power and control of the transducer elements.

There have been developed and commercialized smaller, more portable scanning systems, such as having the size of lap top computers (portable) or even hand-held tablets (ultraportable), however these portable units have suffered from some drawbacks. Although these units allow the ultrasound scanning of a patient to occur in locations that are not dedicated for ultrasound scanning, including at the hospital bedside or other locations, most of these portable systems operate on battery power carried in the portable or hand-held unit, allowing for limited power available for the scanner probes, and leading to a reduced number of transducer elements in the probes. This reduced number of transducer elements results in a reduced resolution of the image typically displayed on the small screen of the portable unit.

One approach that has been provided has been to dedicate a particular probe with the ultrasound scanner control module with a fixed connection, however, this limits the use of the ultrasound scanning system to one particular type of scanning, and requires other scanning systems to perform other types of scanning.

Further, if medical personnel wish to be able to perform many different types of scans with portable scanning systems, they are required to carry a number of different probes with them, with each probe having a probe cable connected thereto, the probe cables each having a length of at least a meter (39 inches) or more. This results in a very bulky collection of equipment necessary to be able to conduct several different types of ultrasound scans.

Another disadvantage is that some conventional scanning systems use complex multiple coaxial cables having 128-256 composite interconnection elements for delivering electrical signals from the corresponding transducer probes. The connectors for connecting the coaxial cables to the conventional scanning systems are rather large and often cannot be accommodated in the smaller hand-held units.

To overcome this problem, some available units place some of the ultrasound electronics in the probe, including a beam former, however, this results in other problems, such as a larger and heavier probe, high heat in the probe due to the electronics, and more expensive probes with electronics located in each probe.

The power supply required for operating large probes (with 128 to 256 transducer elements) is also typically comparatively large, which requires a larger amount of electrical power to be supplied to the probe.

Therefore, there is a need for developing an improved portable medical scanning system having a probe that is efficiently and readily interchangeable during the diagnostic imaging process, is relatively small, lightweight and reasonably priced, and allows for a high quality scanned image.

SUMMARY OF THE INVENTION

Advantages are achieved by the present portable medical scanning system which includes an interchangeable probe connected to a hand-held or portable base unit which contains ultrasound electronics of a complete ultrasound scanning system. An important aspect of the present portable medical scanning system is an interchangeable probe that is easily connectable and removable (e.g., a plug and play system) to and from the base unit at a proximal end of a connecting cable relative to the probe. Different probes are readily quickly installed and removed during or between medical exams as desired, and at a location close to the actual scanning location rather than at the scanning equipment. In this manner, the medical personnel are not required to carry cables for each probe to be used, greatly reducing the bulk of equipment to be carried by the medical personnel. The specific type of probes connected to the base unit are automatically detected by the ultrasound electronics so that the correct types of signals are transmitted to a particular type of probe.

Another important advantage of the present interchangeable probe is that a multiplexer is provided in the probe to allow the number of separate shielded wires in the cable to be reduced by a predetermined factor. In this configuration, while a high number of transducer elements are maintained in the probe (e.g., up to 256), the number of shielded wires can be significantly reduced (by a factor of up to 8) by the use of multiplexing switches of the multiplexer. As a result, the cable becomes thinner (fewer wires to transmit the signals) and easier to handle, and the probe consumes a lower amount of electric power. Further, a beamformer portion of the ultrasound electronics is disposed in the hand-held or portable base unit rather than in the probe, thereby reducing the power consumption at the probe, and also reducing a weight, size and cost of an individual probe.

In one embodiment, a portable scanning system is provided for performing a diagnostic ultrasound scanning process of a patient, or other object being scanned. The scanning system comprises a portable housing containing ultrasound electronics of a complete ultrasound scanning system including a beamformer that regulates and controls operation of the scanning system. A user interface is accessible at the portable housing. A cable is attached at one end to the portable housing and at a second end it has a connector. An interchangeable probe having a plurality of piezoelectric transducer elements is interchangeably coupled to the connector for transmitting electrical signals between ultrasound electronics in the housing and the transducer elements of the interchangeable probe.

In an embodiment, the connector and the probe comprise first and second members with the first member having an opening dimensioned to matingly receive the second member in a complementary relationship.

In an embodiment, the interchangeable probe includes a locking mechanism for securely and releasably attaching the first and second members together.

In an embodiment, the interchangeable probe includes a blocking mechanism for preventing the second member from being inserted into the opening of the first member in an incorrect orientation.

In an embodiment, the first member has a first connection port in the opening, and the second member has a corresponding second connection port, such that the first and second connection ports are electrically and complementarily coupled to each other for transmitting the electrical signal.

In an embodiment, the first connection port includes an upper male slot and a lower male slot for carrying the electrical signal.

In an embodiment, the second connection port includes an upper female slot and a lower female slot for matingly connecting to the corresponding upper and lower male slots.

In an embodiment, the interchangeable probe includes a multiplexing unit positioned between the cable connector and the plurality of transducer elements for transmitting a plurality of signals to and from a single wire in the cable sequentially and selectively to a plurality of different ones of the transducer elements. The ultrasound electronics includes a sequencer that sends a signal to the probe to select, via a multiplexer switch, a particular transducer element to be energized and the resulting echo received at that transducer element is returned to the ultrasound electronics before the sequencer sends a signal to the probe to select a next transducer element to repeat the process.

In an embodiment, the multiplexing unit is configured to transmit signals to and from a single cable wire to and from up to 8 separate wires connected to individual transducer elements.

In an embodiment, the interchangeable probe, being one of a convex probe, a linear probe and a phased array probe, has a size no greater than about 11.4 cm (4.5 inches) by 8 cm (3.2 inches) and 2.5 cm (1 inch) thick.

In an embodiment, the interchangeable probe is an endocavitary probe and has a size no greater than about 30.5 cm (12 inches) by 4 cm (1.6 inches) and 3 cm (1.2 inches) thick.

In an embodiment, the ultrasound electronics comprises a sensing unit and the interchangeable probe comprises an electronic probe identification, wherein the sensing unit automatically senses a presence of a probe at the cable connector and automatically reads the electronic probe identification, thereby causing the ultrasound electronics to transmit a correct type of signal to the probe only when the probe is attached to the cable connector and to terminate the transmission of ultrasound scanning signals to the cable when no probe is detected as being connected to the cable.

In an embodiment, the housing includes a display configured to display a scanned image.

In an embodiment, an interchangeable probe is provided which is used for performing a diagnostic scanning process of a patient, using a portable housing incorporating a complete ultrasound scanning system. The probe comprises a member housing a plurality of high density piezoelectric transducer elements and having electrical connectors dimensioned to electrically matingly connect with a connector member of a cable coupled to the portable housing.

In an embodiment, a portable ultrasound scanning system is provided for performing a diagnostic ultrasound scanning process of a patient. The system comprises a portable housing containing ultrasound electronics of a complete ultrasound scanning system including a beamformer that regulate and controls operation of the scanning system. A user interface is accessible at the portable housing. A cable is attached at one end to the housing and at a second end has a connector. A plurality of interchangeable probes are provided, each being interchangeably coupled to the connector for transmitting an electrical signal between the ultrasound electronics in the housing and the interchangeable probe.

The foregoing and other aspects and features of the disclosure will become apparent to those of reasonable skill in the art from the following detailed description, as considered in conjunction with the accompanying drawings.

DETAILED DESCRIPTION OF THE PREFERRED EMBODIMENTS

Preferred embodiments of the present disclosure are described below by way of example only, with reference to the accompanying drawings. Further, the following description is merely exemplary in nature and is in no way intended to limit the disclosure, its application, or uses.

As used herein, the term "module," or "unit" may refer to, be part of, or include a programmable integrated circuit, an electronic circuit, a processor (shared, dedicated, or group) and/or memory (shared, dedicated, or group) that execute one or more software or firmware programs, a combinational logic circuit, and/or other suitable components that provide the described functionality.

Although children modules residing in their respective parent modules are shown, the broad teachings of the present system can be implemented in a variety of forms. Thus, while this disclosure includes particular examples and arrangements of the modules, the scope of the present system should not be so limited since other modifications will become apparent to the skilled practitioner.

Exemplary embodiments herein below are directed primarily to medical ultrasound scanning systems. However, the present system can be implemented for other types of ultrasound scanning products or services. Thus, the terms "patient" and "tissue" are used to refer to the objects being scanned, and should be understood to refer also to other types of objects.

Figure 1:
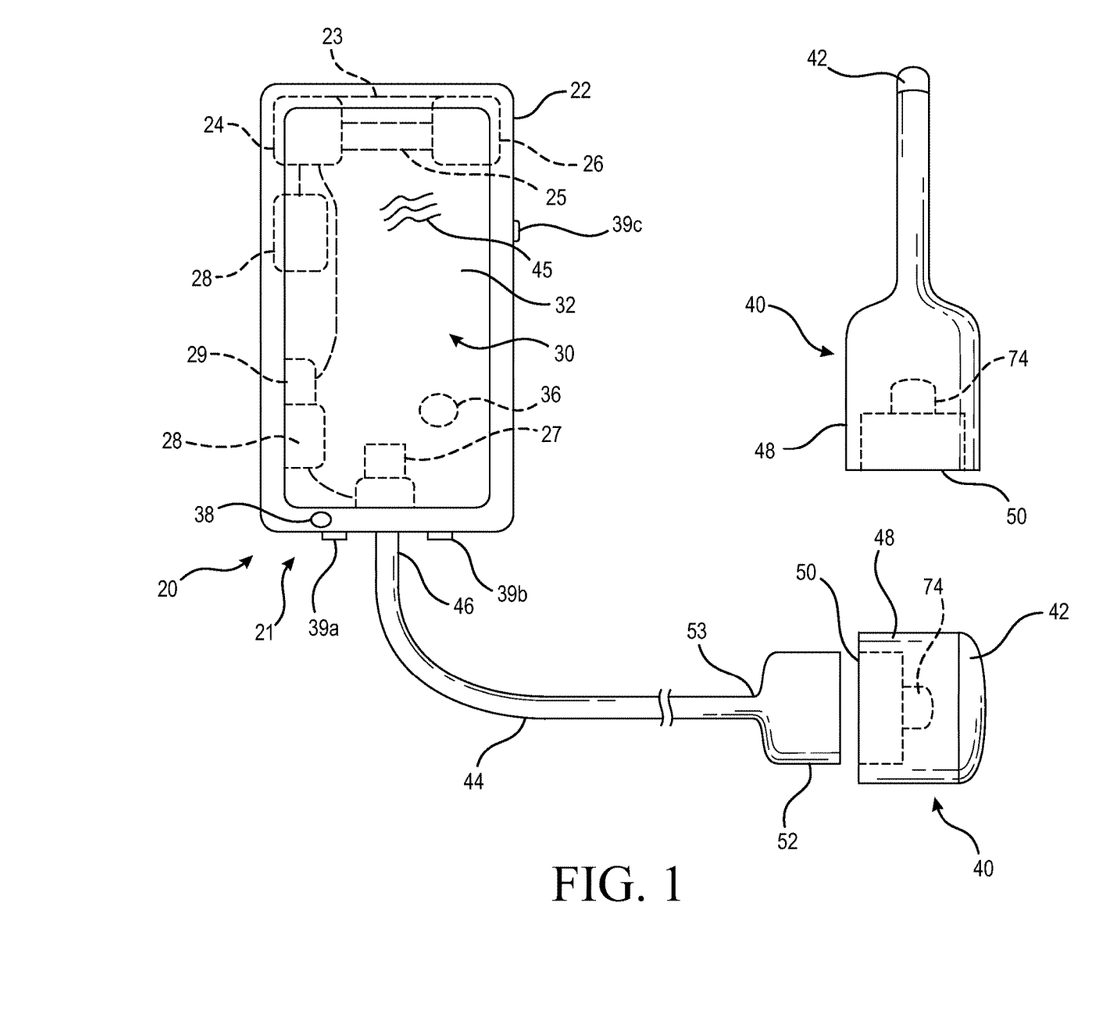
FIG. 1 illustrates an exemplary environment for the present medical scanning system in accordance with an embodiment of the present disclosure.

Referring now to FIG. 1, a portable ultrasound scanning system 20 is illustrated which includes a hand-held housing or base unit 22. In a preferred embodiment, the hand-held housing 22 has a size of approximately 12.7 cm (5 inches) by 17.8 cm (7 inches), with a thickness of about 2 cm (0.9 inches), which allows the housing to fit and easily be carried in a standard size pocket on a medical personnel lab coat. The hand-held housing 22 preferably has a weight of about 600 gm (1.3 pounds) or less. Other sized housings 22 may be used with the present invention, but in a preferred embodiment, the housing has a weight of less than 1000 gm (2.2 pounds), more preferably a weight of less than 800 gm (1.8 pounds) and most preferably, a weight of no more than 600 gm (1.3 pounds).

The hand-held housing 22 contains ultrasound electronics 21 of a complete ultrasound scanner, including a beamformer 23, a central processing unit with a control module 24, a computing unit 25, a memory unit 26, an image processing unit 27, a power supply 28, and an optional wireless transmitter and receiver 29, all electrically interconnected. The ultrasound electronics 21 are configured to contain and operate conventional hardware, firmware and/or software for operating an ultrasound scanner in a known manner and displaying the scanned image on a display, as discussed below.

The power supply 28 preferably comprises a rechargeable battery, such as a lithium polymer battery capable of providing several hours of operation for the ultrasound scanning system 20. Other types of power supplies including line power (alternating current) or other types of power storage devices, including different battery types, may be used as well. It is contemplated that the line power may be used in conjunction with a power converter, such as an AC-DC adapter.

A display 30, which may be a touchscreen 32, is mounted on the hand-held housing 22. In the preferred size of the housing 22 as described above, the display 30 may have a 17.8 cm (7 inch) diagonal size. Larger or smaller displays may be used with the present invention.

A user input interface 36 is provided, at least a part of which is presented on the display 30. The user input interface 36 is configured to receive inputs from the user via the touchscreen 32 and to transmit those inputs to the central processing unit 24.

A variety of different user input interfaces 36 may be utilized within the scope of the present invention. In a preferred embodiment, the user input interface is presented on at least a portion of the touchscreen 32 and can be operated by the user with one or more of the fingers of the hand holding the hand-held housing 22. The user interface 36 may comprise several selectable areas of information or control that may be alternately selectably displayed on the touch screen.

A particular type of user interface is described in more details in co-pending U.S. patent application Ser. Nos. 14/872,616 and 14/872,637, the disclosures of which are incorporated herein by reference. The user input interface 36 may include one or more buttons or switches 38 by means of which the user may activate the portable ultrasound scanning system 20, or provide other inputs to the central processing unit 24 of the ultrasound electronics 21.

Various ports and connectors may be provided in the housing 22, such as a connector 39a for a power supply, a USB port 39b, an HDMI port 39c, as well as ports for other types of connectors.

One or a plurality of interchangeable probes 40 is provided which each contains a plurality of piezoelectric transducer elements 42 controlled by the ultrasound electronics 21. The probe 40 is connected to the housing 22 via a probe cable 44. Detailed descriptions of various types of probes 40 are provided below in paragraphs relating to FIG. 5.

The probe cable 44 may be permanently attached at one end 46 to the housing 22. Alternatively, the probe cable 44 may be detachably attached at the end 46 to the housing 22 via an appropriate connector.

Referring now to FIGS. 2-5, it is preferred that the interchangeable probe 40 includes a first or head member 48 having an opening 50 dimensioned to matingly receive a second or tail member 52 of the cable 44 in a complementary relationship. The tail member 52 is provided at a second end 53 of the cable. The relative sizes and shapes of the head member 48 and the tail member 52 may be reversed in some arrangements, such that the head member 48 is received in an opening in the tail member 52. In a preferred arrangement, the opening 50 of either the head member 48 or tail member 52 is shaped such that the other of the head member or the tail member 52 can be received therein in only one orientation so as to provide a positive mechanical assurance that an improper connection between the head member 48 and the tail member 52 will not occur. While an oval shaped opening 50 is shown in the drawings, the opening may be formed in any other shape as is appropriate for the size and shape of the head member 48 and tail member 52. For example, with the oval shape of the opening 50 shown in the drawings, the tail member 52 could be inserted into the head member 48 in one of two orientations, rotated by 180 degrees around the longitudinal axis. With a square opening there could be four possible orientations and with a circular opening, there could be an infinite number of orientations. To prevent an improper orientation connection, a sidewall of the opening 50 may be provided with a longitudinal ridge 53a that is received in a complementarily shaped longitudinal groove 53b in the tail member. If the head member 48 as illustrated is rotated around its longitudinal axis by 180 degrees the ridge 53a will not find a complementary groove, and therefore the insertion of the tail member 52 into the oval opening 50 of the head member 48 will be positively blocked. Other similar types of blocking arrangements may be provided.

Figure 3:
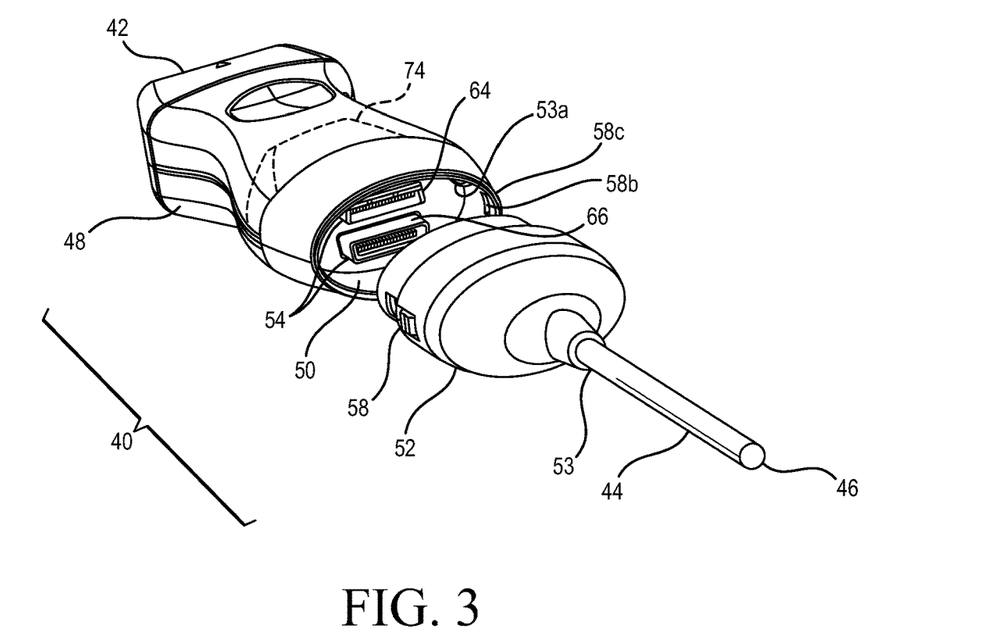
FIG. 3 is a rear view of the interchangeable probe of FIG. 2 before attaching the probe to a connector of the present medical scanning system.
Figure 4:
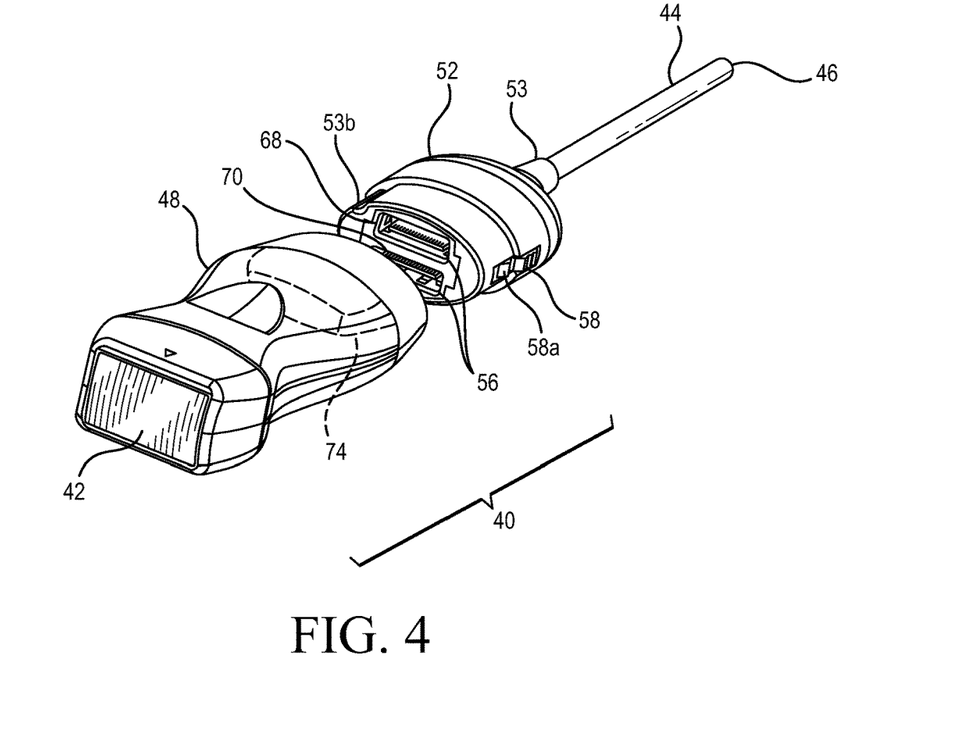
FIG. 4 is a front view of the interchangeable probe of FIG. 3.

In the illustrated embodiment, the head member 48 has a first or male connection port 54 in the opening 50, and the tail member 52 has a corresponding second or female connection port 56, such that the male and female connection ports are electrically and complementarily coupled to each other for transmitting the signals between the probe 40 and the ultrasound electronics 21 when the tail member 52 is inserted into the head member 48. The positions of the male 54 and female 56 connection ports between the head member 8 and the tail member 52 may be reversed in some embodiments.

In a preferred embodiment, a locking mechanism 58 is provided for the probe 40 to securely and releasably attach the head and tail members 48, 52 together. The locking mechanism 58 shown includes a depressible detent 58a carried on the tail member 52 which is received in a slot 58b formed in the sidewall of the opening 50 of the head member 48. The slot 58b has a shoulder 58c near the opening end of the sidewall that engages the detent 58a when the detent is not depressed. Other types of suitable locking mechanisms are also contemplated to suit different applications.

Figure 2:
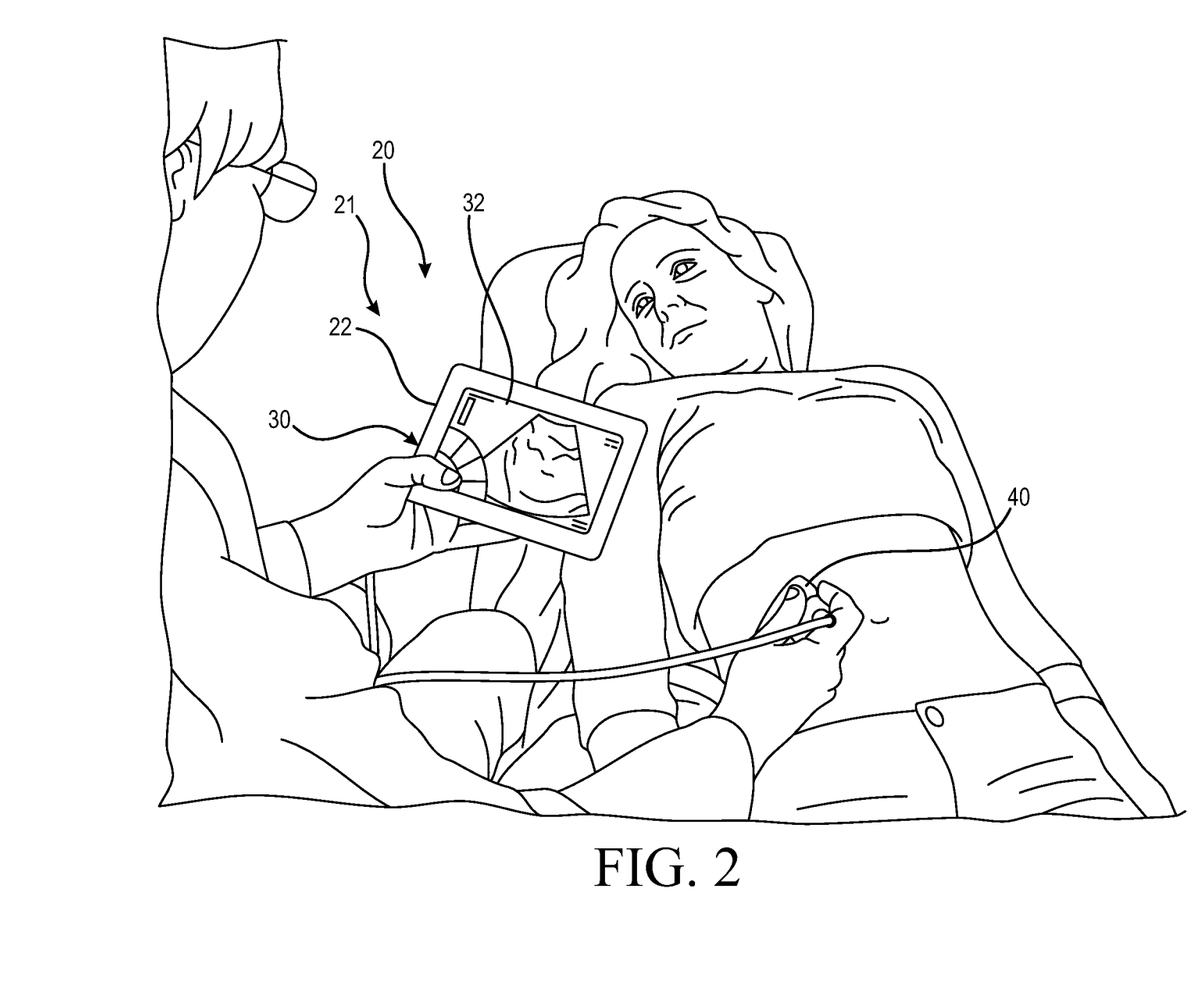
FIG. 2 illustrates an exemplary practice of the present medical scanning system of FIG. 1, utilizing a portable device having a virtual user interface, and an interchangeable probe.

Typically, in conventional piezoelectric ultrasound scanning systems, the probe 40 is interchangeable at the housing end 46 of the connecting cable 44. However, in the present scanning system 20, the probe 40 is interchangeable at the probe end 53 of the connecting cable 44. In this configuration, the head member 48 of the probe 40 is readily interchangeable by the user without having to connect and disconnect the tail member 52 and the connecting cable 44 to and from the housing 22. Thus, different head members 48 are readily and quickly installed and removed or exchanged, during or between medical exams as needed, directly at the location of use of the probe 40.

Figure 5:
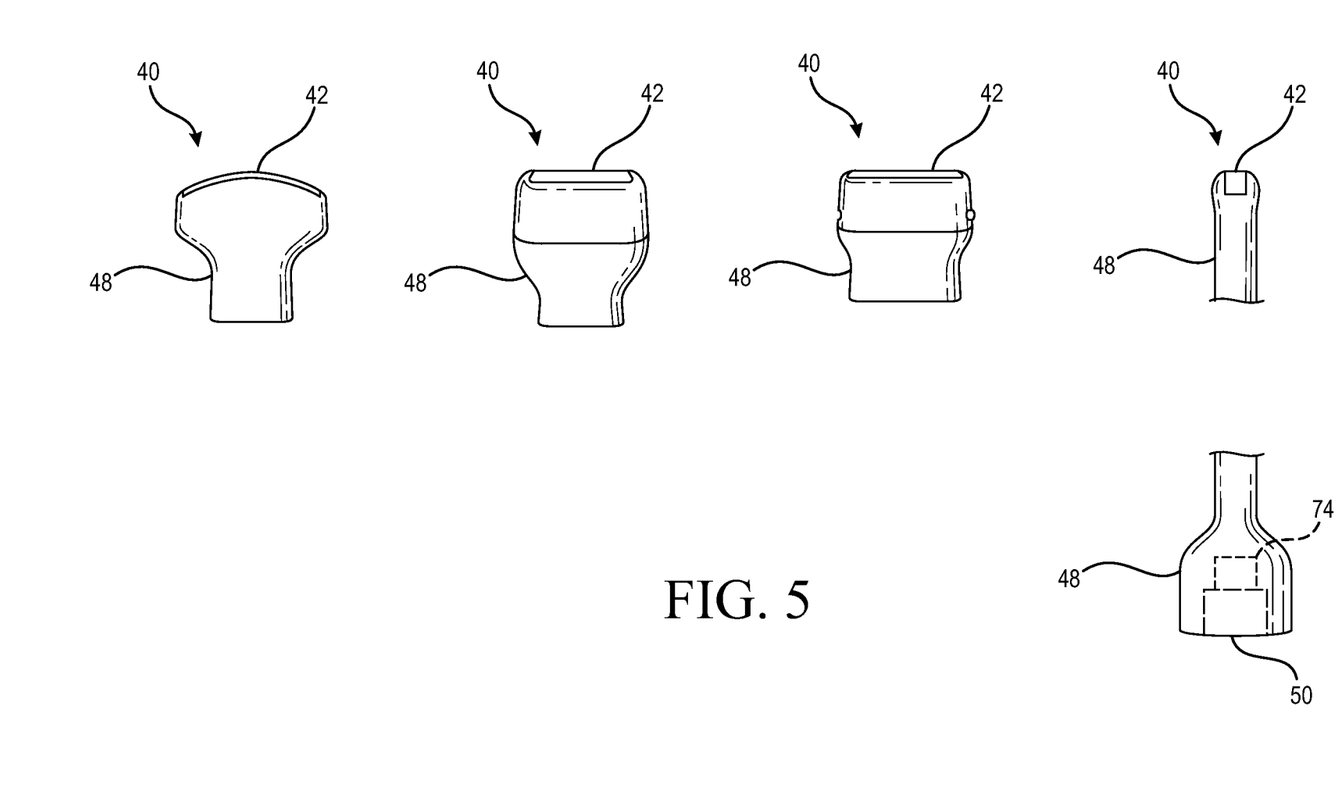
FIG. 5 illustrates various types of exemplary interchangeable probes used with the present medical scanning system of FIG. 1.

As illustrated in FIG. 5, the different head members 48 may include, but are not limited to, a linear probe, a convex probe, an endocavitary probe, a phased array probe, or the like. Other suitable types of probes are also contemplated to suit different applications.

Preferably high density or fine pitch multi-element electronic probes (e.g., 128-256 transducer elements for linear, convex and endocavitary probes or 64 transducer elements for phased array probes) are used as the replaceable probe, such that a high quality image can be produced by the ultrasound scanning system 20. However, while accommodating such a large number of transducer elements, it is advantageous to reduce the number of shielded wires required in the cable 44 and also to minimize the heat generated in the probe 40.

To minimize heat at the probe and to reduce the cost and weight of the probe, the beamformer 23 of the ultrasound electronics 21 is located in the housing 22 rather than in the probe 40. In this configuration, not only the power consumption at the probe 40 is reduced, but also an overall building cost of the probe is lowered without compromising the quality of scanned images 45.

A multiplexing unit 74 comprising a plurality of switches is located on one or more microchips in the head member 48 allowing for a reduction in the number of individual wires needed in the cable 44 for a given number of transducer elements 42. The ultrasound electronics 21 in the housing 22 includes a sequencer that sends a signal to the probe 40 to select, via a switch of the multiplexing unit 74, a particular transducer element 42 to be energized to send out a sound pulse and the resulting echo received at that transducer element 42 is returned to the ultrasound electronics 21 before the sequencer sends a signal to the probe 40 to select a next transducer element 42 to repeat the process. The use of the sequencer in the housing 22 and the switches of the multiplexing unit 74 in the head member 48 allow for an exemplary multiplexing ratio of cable wires to transducer elements 42 to be in the range of 1:1 to 1:8. In this manner, for example, the signals between 256 transducer elements 42 and the ultrasound electronics 21 could be transmitted on as few as 32 wires in the probe cable 44 since the signals between the ultrasound electronics 21 and the transducer elements 42 travel bidirectionally.

It is contemplated that the multiplexing unit 74 is utilized to reduce the diameter of the connecting cable 44 by reducing a number of channels or wires needed for the data transmission, while still maintaining a high number of transducer elements 42. Consequently, the connecting cable 44 becomes substantially thinner or smaller for facilitating easy handling and carrying, as well as a reducing cost of the cable.

In a preferred embodiment, the male connection port 54 further includes an upper male slot 64 having at least 38 contacts in a 15 mm (0.6 inches) length and a separate, lower male slot 66 also having at least 38 contacts in a 15 mm (0.6 inches) length are used, thus providing 76 contacts in a compact area. Similarly, the female connection port 56 further includes a similarly sized upper female slot 68 and a separate, similarly sized lower female slot 70 for matingly connecting to the corresponding male slots 64, 66. In this double slot connection configuration, an overall size of the probe 40 is reduced, thereby enhancing grip ergonomics of the probe. As a result, the double slot configuration of the male and female connection ports 54, 56, along with the multiplexing unit 74, allows for a high number of channels (e.g. up to 64) accommodating a high number of transducer elements (e.g., up to 256) in the probe 40, thereby providing high resolution images 45 for the scanned tissue.

It is advantageous that since only one connecting cable 44 and one tail member 52 are needed for the present system 20, the overall operating cost of the present system with multiple different probes 40 is decreased. Moreover, the overall volume or size of the present system 20 with multiple probes 40 is substantially reduced due to the need for only a single cable 44 with multiple probes 40. Thus, the exemplary configuration of the probe 40 shown in FIGS. 3 and 4 allows production of the high quality images 45 without sacrificing portability and convenience of the ultraportable ultrasound scanning system.

In a preferred arrangement, the interchangeable probe 40, being one of a convex probe, a linear probe and a phased array probe, has a size no greater than about 4.5 inches (11.4 cm) by 3.2 inches (8 cm) and 1 inch (2.5 cm) thick. In an embodiment, the interchangeable probe, being an endocavitary probe, has a size no greater than about 12 inches (30.5 cm) by 1.6 inches (4 cm) and 1.2 inches (3 cm) thick. This allows for several probes 40 to be carried in a single pocket of a lab coat of the medical personnel user.

While at least one exemplary embodiment of the present invention has been shown and described, it should be understood that modifications, substitutions and alternatives may be apparent to one of ordinary skill in the art and can be made without departing from the scope of the invention described herein. This application is intended to cover any adaptations or variations of the specific embodiments discussed herein. In addition, in this application, the terms "comprise" or "comprising" do not exclude other elements or steps, and the terms "a" or "one" do not exclude a plural number. Furthermore, characteristics or steps which have been described with reference to one of the above exemplary embodiments may also be used in combination with other characteristics or steps of other exemplary embodiments described above.

What is claimed is:

1. A portable ultrasound scanning system for performing a diagnostic ultrasound scanning process of a patient, comprising:
   ultrasound electronics of an ultrasound scanning system including a central processing unit, a display comprising a touchscreen and a beamformer that regulate and control operation of the scanning system, and at least 64 high-density piezoelectric transducer elements,
   a portable housing sized no larger than 12.7 cm (5 inches) by 17.8 cm (7 inches) with a thickness of 2 cm (0.9 inches) containing the ultrasound electronics other than the piezoelectric transducer elements;
   a user interface accessible at the housing, at least a portion of the user interface being presented on the display;
   a cable attached at one end to the housing and at a second end having a connector; and an interchangeable probe having the piezoelectric transducer elements being interchangeably coupled to the connector for transmitting electrical signals between the ultrasound electronics in the housing and the transducer elements of the interchangeable probe;

wherein the cable connector has a first connection port including at least two separate multi-contact connectors for carrying the electrical signals, and the interchangeable probe has a corresponding second connection port including at least two separate multi-contact connectors for matingly connecting to the connectors of the cable connector, such that the first and second connection ports are electrically and complementarily coupled to each other for transmitting the electrical signals.

2. The scanning system of claim 1, wherein the connector and the probe comprise first and second members, respectively, with the first member having an opening dimensioned to matingly receive the second member in a complementary relationship.

3. The scanning system of claim 2, wherein the interchangeable probe includes a detent positioned between the first and second members configured to securely and releasably attach the first and second members together.

4. The scanning system of claim 2, wherein the interchangeable probe includes a geometrically shaped projection and recess arranged on the first and second members to prevent the second member from being inserted into the opening of the first member in an incorrect orientation.

5. The scanning system of claim 2, wherein the first member has a first connection port in the opening, and the second member has a corresponding second connection port, such that the first and second connection ports are electrically and complementarily coupled to each other for transmitting the electrical signals.

6. The scanning system of claim 5, wherein the first connection port includes an upper male slot and a lower male slot for carrying the electrical signals.

7. The scanning system of claim 6, wherein the second connection port includes an upper female slot and a lower female slot for matingly connecting to the corresponding upper and lower male slots.

8. The scanning system of claim 1, wherein the interchangeable probe includes an electronic multiplexing unit comprising a plurality of switches and a sequencer positioned between the cable connector and the plurality of transducer elements to transmit a plurality of signals to and from a single wire in the cable sequentially and selectively to a plurality of different ones of the transducer elements.

9. The scanning system of claim 8, wherein the multiplexing unit is configured to transmit signals to and from a single cable wire to and from up to 8 separate wires connected to individual transducer elements.

10. The scanning system of claim 1, wherein the interchangeable probe is one of a convex probe, a linear probe, and a phased array probe and has a size no greater than 11.4 cm (4.5 inches) by 8 cm (3.2 inches) and 2.5 cm (1 inch) thick.

11. The scanning system of claim 1, wherein the interchangeable probe is an endocavitary probe and has a size no greater than 30.5 cm (12 inches) by 4 cm (1.6 inches) and 3 cm (1.2 inches) thick.

12. The portable ultrasound scanning system according to claim 1, wherein the housing includes a display configured to display a scanned image.

13. A portable ultrasound scanning system for performing a diagnostic ultrasound scanning process of a patient, comprising:

ultrasound electronics of an ultrasound scanning system including a central processing unit, a display comprising a touchscreen and a beamformer that regulate and control operation of the scanning system, and at least 64 high-density piezoelectric transducer elements, a portable housing sized no larger than 12.7 cm (5 inches) by 17.8 cm (7 inches) with a thickness of 2 cm (0.9 inches) containing the ultrasound electronics other than the piezoelectric transducer elements;

a user interface accessible at the housing, at least a portion of the user interface being presented on the display;

a cable attached at one end to the housing and at a second end having a connector; and a plurality of interchangeable probes each having the piezoelectric transducer elements and excluding the beamformer, each probe having electrical connectors dimensioned to electrically matingly and interchangeably connect with the connector for transmitting electrical signals between the ultrasound electronics in the housing and the transducer elements of the interchangeable probe, wherein one of the connector and the probe has an opening dimensioned to matingly receive the other of the connector and the probe in a complementary relationship, including a geometrically shaped blocking mechanism in the form of a geometrically shaped projection and recess arranged on the connector and probe to require the connector and the probe to be connected in a single, correct orientation, wherein each of the connector and the probe has at least two multi-contact connection ports for electrically and complementarily coupling with the at least two multi-contact connection ports of the other of the connector and the probe for transmitting the electrical signals, and wherein the interchangeable probe includes an electronic multiplexing unit comprising a plurality of switches and a sequencer positioned between the cable connector and the transducer elements to sequentially and selectively transmit signals to and from a plurality of the transducer elements on a single wire in the cable.

14. The scanning system of claim 13, wherein the interchangeable probe includes a detent positioned between the connector and the probe configured to securely and releasably attach the connector and probe together.

15. The scanning system of claim 13, wherein the multiplexing unit is configured to transmit signals to and from a single cable wire to and from up to 8 separate wires connected to individual transducer elements.

16. The scanning system of claim 13, wherein the interchangeable probe is one of a convex probe, a linear probe, and a phased array probe and has a size no greater than 11.4 cm (4.5 inches) by 8 cm (3.2 inches) and 2.5 cm (1 inch) thick.

17. The scanning system of claim 13, wherein the interchangeable probe is an endocavitary probe and has a size no greater than 30.5 cm (12 inches) by 4 cm (1.6 inches) and 3 cm (1.2 inches) thick.

18. A portable ultrasound scanning system for performing a diagnostic ultrasound scanning process of a patient, comprising:

ultrasound electronics of an ultrasound scanning system including a central processing unit, a display comprising a touchscreen and a beamformer that regulate and control operation of the scanning system, and at least 64 high-density piezoelectric transducer elements, a portable housing sized no larger than 12.7 cm (5 inches) by 17.8 cm (7 inches) with a thickness of 2 cm (0.9 inches) containing the ultrasound electronics other than the piezoelectric transducer elements;

a user interface accessible at the housing, at least a portion of the user interface being presented on the display;

a cable attached at one end to the housing and at a second end having a connector; and an interchangeable probe having the piezoelectric transducer elements being interchangeably coupled to the connector for transmitting electrical signals between the ultrasound electronics in the housing and the transducer elements of the interchangeable probe;

wherein the connector and the probe comprise first and second members, respectively;

wherein one of the connector and the probe has an opening dimensioned to matingly receive the other of the connector and the probe in a complementary relationship, including a geometrically shaped blocking mechanism in the form of a geometrically shaped projection and recess arranged on the first and second members to prevent the connector and the probe from being connected in an incorrect orientation;

wherein the interchangeable probe includes a detent positioned between the first and second members configured to securely and releasably attach the first and second members together;

wherein the interchangeable probe includes an electronic multiplexing unit comprising a plurality of switches and a sequencer positioned between the cable connector and the transducer elements to sequentially and selectively transmit signals to and from a plurality of the transducer elements on a single wire in the cable;

wherein the first member has a first connection port including at least two separate multi-contact connectors for carrying the electrical signals, and the second member has a corresponding second connection port including at least two separate multi-contact connectors for matingly connecting to the connectors of the first connection port, such that the first and second connection ports are electrically and complementarily coupled to each other for transmitting the electrical signals.

* * * * *